United States Patent [19]

Asahina et al.

[11] 4,013,731

[45] Mar. 22, 1977

[54] PROCESS FOR THE MANUFACTURE OF SOLANESOL

[75] Inventors: Masako Asahina, Tokyo; Hideki Kato, Kawagoe; Hideaki Fukawa, Fukuoka, all of Japan

[73] Assignee: Nisshin Flour Milling Co., Ltd., Tokyo, Japan

[22] Filed: July 28, 1975

[21] Appl. No.: 599,780

Related U.S. Application Data

[63] Continuation of Ser. No. 352,322, April 17, 1973, abandoned, which is a continuation-in-part of Ser. No. 29,702, July 21, 1972, abandoned.

[30] Foreign Application Priority Data

Apr. 24, 1969 Japan .................. 44-31303

[52] U.S. Cl. .................. 260/643 A; 260/632.5; 260/643 D
[51] Int. Cl.$^2$ .................. C07C 29/00; C07C 29/24
[58] Field of Search .................. 260/643 A

[56] References Cited

UNITED STATES PATENTS 3,526,669   9/1970   Fukawa et al. ............... 260/643 A

FOREIGN PATENTS OR APPLICATIONS 2,019,835   11/1970   Germany ..................... 260/643 A Primary Examiner—Joseph E. Evans
Attorney, Agent, or Firm—Mason, Fenwick & Lawrence

[57] ABSTRACT

Solanesol may be produced from potato leaves by saponifying the fatty matter extracted out of potato leaves, separating the unsaponified portions of the fatty matter, molecular-distilling the unsaponified portion, and then further refining the solanesol fraction of the distillate.

11 Claims, No Drawings

PROCESS FOR THE MANUFACTURE OF SOLANESOL

This is a continuation of application Ser. No. 352,322, filed Apr. 17, 1973, now abandoned, which in turn is a continuation-in-part of Ser. No. 29,702, 7/21/72, now abandoned.

The present invention relates to a process for the manufacture of solanesol which is an all-trans type isoprenyl alcohol.

The solanesol produced by the process of the present invention has a chemical structure represented by the following formula and in which its double bond is of an all-trans configuration;

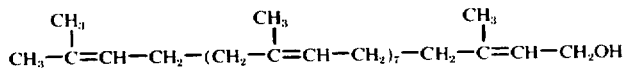

This substance is not only an essential intermediate which is used to synthesize a side chain component of coenzyme Q or vitamin $K_2$ useful as a medicine but it is also useful itself as a medicine or the like. However, this substance has may carbon atoms, has a stereospecificity and is therefore very difficult to produce chemically and synthetically. Further, it has been found that naturally occurring products containing solanesol are few. R. L. Rowland in U.S.A. discovered that solanesol is present in a comparatively large amount in tobacco leaves which are only one solanesol-source commercially utilizable (J. Am. Chem. Soc. 78, 4680, 1956).

It has been found that a solanesol is present in mulberry leaves or silkworm feces and may be recovered therefrom (see, for example, U.S. Pat. No. 3,526,669). However, the solanesol present in mulberry leaves or silkworm feces is at a low content and normally is accompanied by large amount of prenyl alcohols containing 10 to 12 isoprene units. Accordingly, the recovery of solanesol from mulberry leaves or silkworm necessitates complicated separation and purification steps.

We have researched a wide variety of plants, and as a result we have discovered that a solanesol is present in a large amount in potato leaves in a form easy to recover therefrom.

Furthermore, we have succeeded in recovering solanesol from potato leaves and then purifying the solanesol in a simple and efficient manner. According to a first aspect of the present invention, therefore, there is provided a process for producing solanesol from potato leaves comprising: extracting potato leaves with an organic solvent in which the fatty matter of potato leaves is soluble, evaporating off said organic solvent from the resulting organic solvent extract of said fatty matter to give the pasty residue containing said fatty matter, saponifying the fatty matter, separating by extracting the saponified and unsaponified portions, said unsaponified portion containing said solanesol, molecular-distilling the separated unsaponified substance under a vacuum higher than $1 \times 10^{-2}$ mm Hg, collecting the solanesol fraction at 180° to 240° C. and further refining said solanesol fraction by fractionally crystallizing from an organic solvent.

According to a second aspect of the present invention, there is provided a process for producing solanesol from potato leaves comprising: extracting potato leaves with an organic solvent in which the fatty matter of potato leaves is soluble, evaporating off said organic solvent from the resulting organic solvent extract of said fatty matter to give the pasty residue containing said fatty matter, saponifying the fatty matter, separating by extraction the saponified and unsaponified portions, said unsaponified portion containing said solanesol, molecular-distilling the separated unsaponified substance under a vacuum higher than $1 \times 10^{-2}$ mmHg., collecting the solanesol fraction at 180° to 240° C., treating the solanesol fraction with thiourea, separating the thiourea clathrate compound of solanesol formed, reacting said thiourea clathrate compound with water or an aqueous mineral acid, extracting the reaction mixture with a water-immiscible organic solvent in which solanesol is soluble, separating the solanesol fraction from the resulting organic solvent extract and then further refining the solanesol fraction by crystallizing from an organic solvent.

In contrast to mulberry leaves or silkworm feces, the potato leaves have a higher content of solanesol which amounts to 1-3% by weight on the basis of the dry weight of the potato leaves, and advantageously the potato leaves contain substantially none of the other types of isoprenyl alcohol than the all-trans-type isoprenyl alcohol, that is, solanesol.

In carrying out the process according to the first and second aspects of the present invention, the fatty matter of potato leaves is extracted out by extracting the potato leaves, either dried or in green state, with an organic solvent in which the solanesol is soluble. The organic solvent used in this extraction of potato leaves may be a water-immiscible non-polar, organic solvent in which the solanesol is soluble, such as benzene, toluene, hexane and diethylether, and it may also be a polar organic solvent in which solanesol is soluble, such as acetone, ethanol and methanol. The extraction may be conducted in a conventional manner and at room temperature or at an elevated temperature up to the boiling temperature of the solvent employed. This extraction of potato leaves with such an organic solvent affords an organic solvent extract of the fatty matter of potato leaves. The fatty matter is then separated from its organic solvent extract by evaporating off the organic solvent and an amount of water which may be present in said extract. After the evaporation of the organic solvent, the fatty matter remains as the pasty residue.

In the process of the present invention, the fatty matter is then saponified using an alkali such as potassium hydroxide and sodium hydroxide. The saponification of the fatty matter may preferably be carried out by reacting a methanolic solution of an alkali with a solution of the fatty matter in an inert organic solvent such as benzene, n-hexane and isopropyl ether. It is preferred to add an amount of pyrogallol to the solution or dispersion of the fatty matter to be saponified, for the purpose that solanesol can be prevented from being oxidised during the saponification reaction. The reaction may be carried out at room temperature or at an elevated temperature up to the boiling point of the solvent employed. During this saponification of the fatty matter, the solanesol, phytol, higher alcohols, sterins and carotinoid present in the extracted fatty matter remain as the unsaponified matter or portion which is insoluble or sparingly soluble in water, while glycerides and other ethers present in the fatty matter are converted into the saponified matter or portion which is soluble in water. Accordingly, when the reaction mixture which results from the saponification is extracted with water and with a water-immiscible organic solvent in which solanesol is soluble, such as benzene, toluene, hexane, diethylether, the unsaponified portion containing the solanesol fraction is extracted by the organic solvent and isolated from the saponified portion which remains dissolved in the water. The organic solvent extract of the solanesol fraction thus obtained is then subjected to evaporation of the solvent preferably at a reduced pressure to separate the unsaponified portion containing the solanesol.

The separated unsaponified portion is then molecular-distilled under a vacuum higher than $1 \times 10^{-2}$ mmHg, for example, a vacuum of $5 \times 10^{-3}$ to $1 \times 10^{-3}$ mmHg. It is conventional to degas, that is to say, to remove any volatile and gaseous substances from the unsaponified portion by applying a vacuum to the unsaponified portion previously before the molecular-distillation process is conducted.

If the insoluble wax and sterin components are removed from the unsaponified portion by dissolving the unsaponified portion in acetone while leaving the wax and sterin components undissolved as a pretreatment which is carried out before the molecular distillation, the molecular-distilling operation becomes easier and the separation efficiency is improved. Unless the molecular distillation is carried out under a vacuum of higher than $1 \times 10^{-2}$ mmHg, it is impossible to distill solanesol from the unsaponified portion. Under a vacuum of higher than $1 \times 10^{-2}$ mmHg, the desired solanesol fraction begins to distil out at a distilling temperature near 180° C and is distilled between said temperature and about 240° C. For the molecular distillation can be used either a film flow down type or a centrifugal type of molecular distillation apparatus.

When the unsaponified substance of the fatty matter is molecularly distilled in the above-mentioned way, the phytol, higher alcohols, sterins and carotinoids are distilled out as the low boiling point distillates. The solanesol fraction which is distilled out at 180° to 240° C mainly comprises solanesol but still contains minor amounts of sterins, carotinoids and trace amounts of the other types of isoprenyl alcohol and resins.

Therefore, the solanesol fraction must be further refined. For this purpose of further purifying the solanesol fraction, this solanesol fraction may be subjected to fractional crystallization from an organic solvent which is selected from the group consisting of acetone and hexane and mixtures thereof. For this fractional crystallization, the solanesol fraction is dissolved in acetone or hexane or a mixture of acetone and hexane in an amount of 5 to 10 parts by weight per part of the solanesol fraction, and the solution is allowed to stand at a temperature of 0° C to room temperature, whereupon crystalline substances mainly comprising sterins are crystallized. After these crystalline substances are removed by filtration, the mother liquor is concentrated by evaporation of the solvent under a reduced pressure. The concentrated solution so obtained is then allowed to stand at a temperature of minus 5° C to minus 20° C. Pure or substantially pure solanesol is deposited as crystals from the solution and removed by filtration. The solanesol crystals removed are then washed with a small volume of acetone and then dried to give a pure or substantially pure solanesol in a high yield.

For the purpose of further refining the solanesol fraction which has been obtained from the molecular-distillation step, it is also feasible to treat the solanesol fraction with thiourea in solution in benzene or toluene, so that solanesol is converted into the thiourea clathrate compound of solanesol while the impurity components such as sterins remain unchanged. The thiourea clathrate compound of solanesol is deposited owing to its lower solubility from the benzene or toluene solution with leaving the impurity component in solution.

In order to convert solanesol into the thiourea clathrate compound, the treatment of the solanesol fraction with thiourea may be carried out in the following manner: The solanesol fraction is dissolved in an amount of 5 to 20 parts by weight of benzene or toluene per part of the solanesol fraction. To the benzene or toluene solution is added a solution of thiourea in methanol in such proportions that the quantity of the thiourea added is 2 to 10 times higher than the quantity of the solanesol. The admixture so obtained is then well agitated and allowed to stand overnight at a temperature of 0° C to room temperature. The thiourea clathrate compound of solanesol is deposited, removed by filtration and then washed with a small volume of benzene-methanol mixture. The thiourea clathrate compound of solanesol isolated in this way is then suspended in water and the aqueous suspension is agitated for a time during which the thiourea clathrate compound decompose to liberate the free form of solanesol. Heating and/or addition of a mineral acid such as sulfuric acid or hydrochloric acid to the suspension promotes the decomposition of the clathrate compound. The decomposition reaction mixture so obtained is then extracted with a water-immiscible organic solvent in which solanesol is soluble, such as acetone, n-hexane and diethylether. The resulting organic solvent extract is freed from the solvent by evaporation, so that solanesol is left as an oily residue when hot or as a waxy material when cold. The solanesol may subsequently be further purified by crystallizing from an organic solvent which may be acetone, n-hexane or a mixture of acetone and n-hexane.

The solanesol obtained by the present invention gives a single spot on thin film chromatography, gas chromatography and reverse phase filter paper chromatography, coincides with the authentic sample in respect to the infrared absorption spectrum, nuclear magnetic resonance spectrum and melting point and is of such high purity that it is well suitable for use as a starting material for synthesis of the medicines.

The following examples will illustrate the present invention but the invention is not restricted to these examples.

EXAMPLE 1

6000 g. of dried potato leaves were extracted with 50 l. of diethylether at room temperature for 3 hours. After removal of the potato leaves, the ether extract containing the fatty matter of potato leaves was obtained. The diethylether solvent was evaporated off from the ether extract to give 480 g. of the fatty matter as the pasty residue.

This fatty matter was dissolved in 2500 ml of benzene, and the 5 g. of pyrogallol was added to the benzene solution of the fatty matter. A solution of 500 g. of potassium hydroxide in 7500 ml. of methanol was further added thereto. The admixture was allowed to stand overnight during which the saponification of the fatty matter took place. The saponification reaction mixture so formed was extracted with about 7 l. of water and about 7 l. of diethylether added to effect the liquid-liquid extraction. The aqueous phase was separated and discarded, and the diethylether extract was again washed with further 5 l. of water. The aqueous washings were discarded. The diethylether extract was dried by adding about 300 g. of anhydrous sodium sulfate thereto and allowing to stand overnight at room temperature. The sodium sulfate was filtered off, and from the dried diethylether extract containing the unsaponified portion of the fatty matter was evaporated the ether solvent to give 360 g. of the unsaponified portion of the fatty matter which contained solanesol.

This unsaponified portion of the fatty matter was well degassed by applying a vacuum thereto. The unsaponified matter was then molecular-distilled in a centrifugal type molecular-distilling apparatus under a vacuum of $5 \times 10^{-3}$ to $8 \times 10^{-3}$ mmHg. At temperatures up to 180° C, low boiling fractions comprising phytol and sterins were distilled out. The solanesol fraction which distilled out in a temperature range of from 180° C to 240° C at a vacuum of $5 \times 10^{-3}$ to $8 \times 10^{-3}$ mmHg was collected in a yield of 120 g. When this solanesol fraction was analyzed by a silica gel thin layer chromatography, it was found that this fraction contained minor amounts of sterins and carotinoid in addition to the solanesol.

120 g. of the solanesol fraction which resulted from the molecular-distillation step was dissolved in about 1000 ml. of acetone, and the acetone solution was allowed to stand overnight at a temperature of 5° C and crystalline substance deposited from the solution. The crystalline substance (mainly comprising sterins) was filtered off. The filtrate was concentrated to a half-volume and the concentrated solution was allowed to stand overnight at a temperature of −15° C to deposit solanesol which was then filtered off, washed with a small volume of acetone and dried under a reduced pressure. A yield of 66 g. of solanesol in the form of a crystalline, pure product was obtained as a first crop. The mother liquor was again concentrated to a half-volume and then allowed to stand overnight at a temperature −15° C to deposite solanesol which was collected in the same manner as the first crop. 24 g. of solanesol was obtained as a second crop. The total yield of solanesol was 90 g.

EXAMPLE 2

The fatty matter of potato leaves was extracted and saponified in the same manner as in Example 1. The unsaponified matter was then separated and molecular-distilled in the same manner as in Example 1.

120 g. of the molecular-distilled solanesol fraction thus obtained in the same manner as in Example 1 was dissolved in 500 ml. of benzene. This benzene solution was dropped at 30° C under stirring into a solution of 300 g. of thiourea in 1000 ml. of methanol. The admixture was left at 0° to 5° C overnight. The thiourea clathrate compound of solanesol deposited and was filtered, and it was decomposed with water added. The decomposition reaction mixture was extracted with diethylether, and the diethylether extract was evaporated to remove the solvent so that about 60 g. of solanesol was obtained as an oil. When this solanesol product was examined by a thin film chromatograph, it was found to be substantially pure solanesol. When 60 g. of this solanesol product was dissolved in a 5-fold quantity of acetone and then crystallized at 0° C, 50 g. of solanesol of a higher purity were obtained.

EXAMPLE 3

60 g. of dried potato leaves was extracted with 500 ml. of n-hexane at room temperature for 10 hours. From the n-hexane extract was the n-hexane solvent to give 2.4 g. of the fatty matter of potato leaves as a pasty residue. In a further experiment, 60 g. of dried potato leaves was extracted with 500 ml. of acetone at 35° C for 5.5 hours. From the acetone extract was evaporated the acetone to give 5.1 g. of the fatty matter as a pasty residue. Further 50 g. of dried potato leaves was extracted with 700 ml. of methanol for 2.5 hours on a steam bath under reflux. The methanol extract was then distilled in vacuo to remove the methanol, so that 2.8 g. of the fatty matter remained as a pasty residue. Again, 50 g. of dried potato leaves was extracted with 400 ml. of benzene at room temperature for 3 hours. The benzene extract was distilled in vacuo to remove the benzene, so that 2.7 g. of the fatty matter was left as a pasty residue.

All grades of the fatty matter so obtained were processed in the same manner as in Example 1 to give solanesol products of high purity.

What we claim is:

1. A process for producing solanesol from potato leaves comprising: extracting potato leave with an organic solvent in which the fatty matter of potato leaves is soluble, evaporating off said organic solvent from the resulting organic solvent extract of said fatty matter to give the pasty residue containing said fatty matter, saponifying the fatty matter, separating by extraction the saponified and unsaponified portions, said unsaponified portion containing said solanesol, molecular-distilling the separated unsaponified substance under a vacuum higher than $1 \times 10^{-2}$ mmHg, collecting the solanesol fraction at 180° to 240° C. and further refining said solanesol fraction by fractionally crystallizing from an organic solvent.

2. A process for producing solanesol from potato leaves comprising: extracting potato leaves with an organic solvent in which the fatty matter of potato leaves is soluble, evaporating off said organic solvent from the resulting organic solvent extract of said fatty matter to give the pasty residue containing said fatty matter, saponifying the fatty matter, separating by extraction the saponified and unsaponified portions, said unsaponified portion containing said solanesol, molecular-distilling the separated unsaponified substance under a vacuum higher than $1 \times 10^{-2}$ mmHg., collecting the solanesol fraction at 180° to 240° C., treating the solanesol fraction with thiourea, separating the thiourea clathrate compound of solanesol formed, reacting said thiourea clathrate compound with water or an aqueous mineral acid, extracting the reaction mixture with a water-immiscible organic solvent in which solanesol is soluble, separating the solanesol fraction from the resulting organic solvent extract and then further refining the solanesol fraction by crystallizing from an organic solvent.

3. A process as claimed in claim 1 in which the organic solvent used in the extraction of potato leaves is a water-immiscible organic solvent selected from the group consisting of benzene, toluene, n-hexane and diethylether.

4. A process as claimed in claim 1 in which the organic solvent used in the extraction of potato leaves is a polar solvent selected from the group consisting of acetone, ethanol and methanol.

5. A process as claimed in claim 1 in which the saponification of the fatty matter is conducted using an alkali, and the saponification reaction mixture formed is extracted with water and a water-immiscible organic solvent in which solanesol is soluble, the resulting organic solvent solution containing the unsaponified portion is removed and then distilled to separate the unsaponified portion which is subsequently molecular-distilled.

6. A process as claimed in claim 1 in which the organic solvent used in the fractional crystallization is taken from the group consisting of hexane, acetone and mixtures thereof.

7. A process as claimed in claim 2 in which the treatment of the solanesol fraction with thiourea is carried out using 2–10 parts by weight of thiourea for one part by weight of the solanesol fraction.

8. A process as claimed in claim 2 in which the organic solvent used in the crystallization for the further refining of the solanesol is taken from the group consisting of hexane and acetone and mixtures thereof.

9. The process claimed in claim 1 wherein the organic solvent for extracting the potato leaves is selected from the group consisting of benzene, toluene, hexane, diethylether, acetone, ethanol and methanol and wherein the extraction of the potato leaves with the organic solvent is at a temperature of up to the boiling temperature of the solvent, said organic solvent for fractionally crystallizing is selected from the group consisting of acetone, hexane and mixtures thereof, and the temperature of the fractional crystallization is in the range of from minus 20° C to room temperature.

10. The process claimed in claim 2 wherein the organic solvent for extracting the potato leaves is selected from the group consisting of benzene, toluene, hexane, diethylether, acetone, ethanol and methanol and wherein the extraction of the potato leaves with the organic solvent is at a temperature of up to the boiling temperature of the solvent, said organic solvent for fractionally crystallizing is selected from the group consisting of acetone, hexane and mixtures thereof, and the temperature of the fractional crystallization is in the range of from minus 20° C to room temperature.

11. The process as defined in claim 10 wherein the aqueous mineral acid is selected from the group consisting of sulfuric acid and hydrochloric acid and the water-immiscible organic solvent is selected from the group consisting of acetone, n-hexane and diethylether and the fractionally crystallizing temperature is in the range of from minus 20° C to room temperature.

* * * * *